United States Patent [19]

Bremer et al.

[11] 4,365,069

[45] Dec. 21, 1982

[54] USE OF IMPROVED MIXED VANADIUM PHOSPHORUS OXIDE CATALYST IN OXIDATION PROCESSES

[75] Inventors: Noel J. Bremer, Kent; Dennis E. Dria, Cleveland Heights; Andrew M. Weber, Bedford Heights, all of Ohio

[73] Assignee: The Standard Oil Company, Cleveland, Ohio

[21] Appl. No.: 286,434

[22] Filed: Jul. 24, 1981

[51] Int. Cl.$^3$ .............................................. C07D 307/60
[52] U.S. Cl. ................................... 549/260; 549/259; 252/437
[58] Field of Search .................... 260/346.75; 549/259, 549/260

[56] References Cited

U.S. PATENT DOCUMENTS

| | | | |
|---|---|---|---|
| 4,002,650 | 1/1977 | Bremer et al. | 260/346.75 |
| 4,016,105 | 4/1977 | Kerr | 252/437 |
| 4,043,943 | 8/1977 | Schneider | 252/437 |
| 4,132,670 | 1/1979 | Katsumoto et al. | 252/437 |
| 4,147,661 | 4/1979 | Higgins et al. | 252/435 |
| 4,244,879 | 1/1981 | Bremer et al. | 260/346.75 |

FOREIGN PATENT DOCUMENTS 3431 8/1979 European Pat. Off. .

*Primary Examiner*—Henry R. Jiles
*Assistant Examiner*—Bernard Dentz
*Attorney, Agent, or Firm*—Joseph G. Curatolo; Herbert D. Knudsen; Larry W. Evans

[57] ABSTRACT

Vanadium phosphorus mixed oxide containing catalysts are prepared in an organic liquid reaction medium with heating wherein at least 1.5 moles organic liquid are removed from the reaction medium such as by distillation for each mole of vanadium which is reduced or reacted during such reaction and/or reduction. The resulting catalysts are useful for the production of maleic anhydride from 4 carbon atom hydrocarbons.

10 Claims, No Drawings

USE OF IMPROVED MIXED VANADIUM PHOSPHORUS OXIDE CATALYST IN OXIDATION PROCESSES

BACKGROUND OF THE INVENTION

This invention relates to a method for preparing catalysts useful in the production of dicarboxylic acid anhydrides by the oxidation of hydrocarbons. More particularly it is directed to the preparation of catalysts suitable for producing maleic anhydride from 4-carbon atom hydrocarbons, such as n-butane, n-butenes, 1,3-butadiene or a mixture thereof.

Catalysts containing vanadium and phosphorus oxides have been used in the oxidation of 4-carbon atom hydrocarbons, such as n-butane, n-butenes, 1,3-butadiene or mixtures thereof with molecular oxygen or oxygen-containing gas to produce maleic anhydride. Conventional methods of preparing these catalysts involve reducing a pentavalent vanadium compound, and combining the same with a phosphorus compound, and if desired, promoter element compounds under conditions which will provide or maintain vanadium in a valence state below +5 to form catalyst precursors capable of being converted to an oxide. The catalysts oxide precursor is then recovered and calcined to provide active catalytic material.

The use of gaseous HCl as a reducing agent for vanadium is disclosed in U.S. Pat. No. 4,002,650 where the vanadium and phosphorus components are reacted in an aqueous solution. The use of gaseous HCl as a reducing agent for vanadium is also described in U.S. Pat. No. 4,043,943 where the vanadium and phosphorus components are reacted in liquid organic medium.

U.S. Pat. No. 4,016,105 describes the preparation of vanadium and phosphorus oxide-containing catalysts, utilizing as reducing agents, organic acid or aldehydes, together with a co-reducing secondary alcohol. These reducing agents are added to an aqueous solution with the vanadium and phosphorus components.

Similar preparational techniques are described in European Patent Application Ser. No. 3,431 in which the additional step of comminuting the vanadium-phosphorus precursor to a particle size of 500 to 700 microns (0.5 to 0.7 mm) is disclosed.

The use of such reducing agents as disclosed in the art, requires special precautions in the preparation of these catalysts because of the corrosive nature of the materials utilized. The process of the present invention permits the preparation of mixed vanadium phosphorus oxide catalyst without the use of corrosive reducing agents.

A method for preparing catalysts containing vanadium and phosphorus oxides was described in U.S. Pat. No. 4,132,670 which required the maintenance of a solid phase and dispersion of the vanadium-containing feed compound. The method includes forming a vanadium-containing compound dispersion in an organic liquid medium such as alcohols, aldehydes, ketones, ethers or mixtures thereof, heating the dispersion to reduce the vanadium, and thereafter adding phosphoric acid in an organic solvent.

The preparation of oxidation catalysts containing the mixed oxides of vanadium and phosphorus is disclosed in U.S. Pat. No. 4,244,879 wherein a vanadium compound is at least partially solubilized in an organic liquid medium capable of reducing at least a portion of the vanadium to a +4 valence state, and unsolubilized vanadium having a particle size larger than about 0.1 mm diameter is removed from the medium before addition of a phosphorus-containing compound.

The preparation of vanadium phosphorus mixed oxide containing catalyst is disclosed in co-pending U.S. Ser. No. 146,971, assigned to our common assignee, wherein partial reduction of a pentavalent vanadium compound is effected in the presence of a phosphorus compound in an organic liquid medium capable of reducing the vanadium.

Co-pending U.S. Ser. No. 220,629, also assigned to our common assignee, discloses the preparation of vanadium phosphorus oxide catalysts utilizing a mixed phosphorus component compound source, preparing the catalyst in a liquid medium capable of reducing the vanadium component.

DISCLOSURE OF THE INVENTION

In the preparation of vanadium phosphorus mixed oxide catalysts utilizing organic liquid reaction media, it had previously been known to remove excess water formed as a result of the reaction of vanadium by utilizing a Dean-Stark receiver. Such devices at least partially remove the aqueous phase from the reaction medium, by evaporation, returning condensed organic phase to the reaction media.

We have found, however, that vanadium phosphorus mixed oxide catalysts having enhanced activity for oxidation reactions, such as the production of maleic anhydride from 4-carbon atom hydrocarbons such as n-butane, are prepared in organic liquids capable of reducing the valence state of at least a portion of pentavalent vanadium to +4, particularly alcohols and glycols, by reacting the vanadium component and phosphorus component in the organic liquid containing reaction medium, preferably with heating, and removing at least about 1.5 moles of the organic liquid per mole of vanadium reacted.

It is therefore an object of the invention to provide a process of preparing vanadium and phosphorus-containing catalysts useful for the oxidation of 4-carbon atom hydrocarbons to produce maleic anhydride, which catalysts exhibit excellent yields and selectivity to maleic anhydride.

It is a further object of the invention to provide a process of preparing vanadium and phosphorus-containing catalyst useful for the oxidation of 4-carbon atom hydrocarbons to produce maleic anhydride which is simplified, highly reproducible, and economical; which avoids the hazards of corrosion, and which is capable of commercial scale-up.

In general, the process of the present invention includes (a) introducing a pentavalent vanadium compound into an organic liquid reaction medium selected from alcohols and glycols capable of reducing at least a portion of the vanadium to a valence state of about +4 in the absence of corrosive reducing agents;

(b) introducing at least one pentavalent phosphorus compound into the reaction medium;

(c) effecting reduction of the vanadium prior or subsequent to the addition of the phosphorus compound and reacting the vanadium with the phosphorus compound to form a catalyst precursor, (d) removing from the reaction medium at least 1.5 moles pf the organic liqud per mole of vanadium reduced or reacted during the reduction or reaction;

(e) recovering the catalyst precursor from the reaction medium;

(f) drying the catalyst precursor;

(g) calcining the catalyst precursor.

The catalysts prepared by the above process are particularly effective in the oxidation of 4-carbon atom hydrocarbons such as n-butane, n-butenes, 1,3-butadiene or mixtures thereof with molecular oxygen or an oxygen-containing gas in the vapor phase to produce high yields of maleic anhydride with high selectivity. Essentially all the product produced in this oxidation process is maleic anhydride, with only minor amounts of lower acids being detected.

DETAILED DESCRIPTION OF THE INVENTION

In the process for the preparation of an oxidation catalyst containing the mixed oxides of vanadium and phosphorus, a vanadium compound, particularly a pentavalent vanadium compound, is introduced into a liquid reaction medium capable of reducing the valence state of the vanadium. Suitable vanadium compounds containing pentavalent vanadium include: vanadium pentoxide or vanadium salts, such as ammonium metavanadate. Vanadium pentoxide is preferred.

According to a preferred method of the present invention, at least one phosphorus-containing compound is added to the reaction medium before substantial reduction of the vanadium to a valence state less than $+5$ is effected. The phosphorus compounds utilized in the process of the invention are preferably pentavalent and suitable phosphorus compounds containing pentavalent phosphorus include: phosphoric acid, phosphorus pentoxide or a mixed pentavalent phosphorus component comprising a mixture of orthophosphoric acid and pyrophosphoric acid. Optionally, minor amounts of higher polyphosphoric acid may be included. The phosphorus component mixture should comprise about 45 to about 90 percent orthophosphoric acid, about 10 to about 50 percent pyrophosphoric acid, and 0 to about 10 percent triphosphoric acid and higher polyphosphoric acids, percentages being based upon weight of total phosphoric acids. As hydrolysis is a factor in determining the ratio of orthophosphoric acid to pyrophosphoric acid when present in aqueous solution, the above weight ratios are significant provided an extended period of hydrolysis has not occurred to convert the pyrophosphoric acid and higher polyphosphoric acids to the orthophosphoric form.

The phosphorus-containing compound or compounds may be added to the vanadium/liquid reaction medium in the form of a solution of the phosphorus component in either a component of the liquid reaction medium, or in a liquid capable of yielding the phosphorus component to the liquid reaction mixture. Alternatively, a vanadium compound and a phosphorus compound, such a 100% phosphoric acid, may be introduced simultaneously into the liquid reaction medium. In yet another mode, the vanadium compound is introduced into a solution or dispersion of the phosphorus component in the liquid reaction medium.

It is preferred that the vanadium-containing compound which is introduced into the liquid medium have a small particle size, and methods for further reducing particle size of the vanadium compound while in the liquid medium, such as by ball milling the initial suspension of vanadium in the liquid medium, may be employed.

The organic liquid medium employed in the process of the present invention must be capable of reducing at least a portion of the vanadium to a $+4$ valence state, preferably upon mixing and heating. In addition, the liquid medium should be a solvent for phosphoric acid and be relatively unreactive towards phosphoric acid. The liquid medium should not, however, be a solvent for the mixed oxide precursor of vanadium and phosphorus and thus the medium is maintained free of corrosive reducing or solubilizing agents such as HCl, HBr and oxalic acid. Suitable liquid media for use in the invention include alcohols and glycols and are preferably anhydrous. Examples of organic liquids suitable for use in this invention are isobutanol and ethylene glycol.

After the pentavalent vanadium compound is introduced into the liquid reaction medium, reduction of the vanadium is effected either prior to or subsequent to the addition of the phosphorus component to the liquid reaction medium. The reduction is preferably effected by heating the reaction medium, with stirring if desired. Preferred vanadium and phosphorus oxide catalysts for the oxidation of 4-carbon atom hydrocarbons to maleic anhydride contain vanadium in an average valence state of about $+3.5$ to about $+4.6$. This average valence state is achieved when at least a portion of the pentavalent vanadium introduced into the reaction mixture is reduced to the $+4$ state. The average valence state of the vanadium is reduced preferably to about $+4.1$. After partial reduction of the vanadium, in one embodiment of the invention where reduction is effected prior to the addition of the phosphorus component to the reaction medium, large particle unsolubilized vanadium-containing compounds may be removed from the reaction mixture as taught in U.S. Pat. No. 4,244,879.

According to the process of the present invention, the reduction of the pentavalent vanadium is carried out in the organic liquid reaction medium with heating, preferably under reflux conditions, and preferably in the presence of the phosphorus component. Vanadium phosphorus mixed oxide catalysts having improved activity for the oxidation of 4-carbon atom hydrocarbons such as n-butane are obtained when a portion of the organic liquid is removed from the reaction medium during the reduction reaction of vanadium, and/or the reaction of vanadium and the phosphorus component. Such removal is preferably effected by distillation. At least 1.5 moles organic liquid per mole of vanadium reacted should be removed during the reaction of vanadium, and removal of 1.5 moles to about 15 moles of organic liquid per mole of vanadium reacted is preferred.

The removal of the organic liquid such as by distillation effects the removal not only of the initial organic liquid utilized, but additionally effects the removal of byproduct liquids of the reaction, such as water, aldehydes and other oxidation products of the organic liquid utilized. The number of moles of organic liquid to be removed, therefore, should be deemed to include the number of moles of byproduct organic liquids which would also be removed. It is preferred that the removal of the organic liquid and byproducts commence as soon as practicable upon the initiation of the reaction of the vanadium.

The vanadium phosphorus catalyst precursor which is formed in the process of the present invention is a finely divided precipitate or powder. The catalyst precursor, when dried, forms a freely flowing powdery to granular solid, suitable for economical and commercial processing. After the catalyst precursor is formed, it is recovered from the reaction medium by conventional methods including evaporation, filtration, centrifugation and decantation. The catalyst precursor or catalyst precursor precipitate is dried and thereafter calcined.

It is within the scope of this invention, to include promoter element-containing compounds in the reaction mixture at a suitable point, either prior to or subsequent to reduction of the vanadium, in order that the catalyst precursor or catalyst precursor precipitate contain the promoter element. Suitable promoters include but are not limited to U, Co, Mo, Fe, Zn, Hf, Zr or mixtures thereof.

Catalysts prepared by the method of this invention exhibit a phosphorus to vanadium ratio of about 0.9:1 to about 1.3:1. The catalyst is calcined in an inert atmosphere, air or an oxygen-containing gas at a temperature of about 250° C. to about 600° C., generally for a period of up to 5 hours or more. Calcination of the catalyst may be accomplished by heating the catalyst in a mixture of steam and air or air alone over the catalyst at a temperature of about 300° C. to about 500° C. for a period generally of about 1 to 5 hours. The catalyst may also be calcined either in the presence of hydrocarbon, an inert gas, or both.

The hydrocarbon reacted to form maleic anhydride may be n-butane, the n-butenes, 1,3-butadiene or a mixture thereof. Preferred is the use of n-butane or a mixture of hydrocarbons that are produced in refinery streams. The molecular oxygen needed for the reaction to produce maleic anhydride is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of molecular oxygen to the hydrocarbon may range from about 3 to about 30 moles of oxygen per mole of hydrocarbon. Preferred oxygen/hydrocarbon ratios are about 4 to about 20 moles of oxygen per mole of hydrocarbon.

The reaction temperature may vary widely and is dependent upon the particular hydrocarbon and catalyst employed. Normally, temperatures of about 250° C. to about 600° C. are employed with temperatures of about 325° C. to about 475° C. being preferred.

The catalyst may be used alone or a support could be employed. Suitable supports include silica, alumina, Alundum, silicon carbide, titania, boron phosphate, zirconia, and the like. The catalyst may be used in a fixed-bed reactor using tablets, pellets or the like, or in a fluid-bed reactor using catalysts prepared such as by spray drying, and preferably having a particle size of less than about 300 microns. The contact time may be as low as a fraction of a second or as high as 50 seconds. The reaction may be conducted at atmospheric, superatmospheric, or subatmospheric pressure.

SPECIFIC EMBODIMENTS OF THE INVENTION

Examples 1-3

Catalysts of the formula $V_1P_{1.2}O_x$ (wherein x is the number of oxygens required to satisfy the valence of the other elements) were prepared as follows.

909.5 g $V_2O_5$ and 1384 g $H_3PO_4$ (85%) were introduced into 16 liters isobutanol with stirring. The reaction mixture was heated to reflux, and distillation of the organic liquid was commenced and continued until about 9 liters were removed. Reflux was continued for about 9 hours. The resulting catalyst precursor was removed from the reaction mixture by filtration and was dried for about 2 hours at 150° C. The dried precursor was calcined in air for one hour at 400° C. The resulting catalyst was processed with 3% stearic acid to form 3/16 inch (0.48 cm) tablets.

Comparative Examples 4-5

Catalysts of the formula $V_1P_{1.2}O_x$ were prepared according to the procedure of Examples 1-3, except that the reaction mixture was not subjected to distillation.

Example 6

A catalyst of the formula $V_1P_{1.2}O_x$ was prepared by the procedure of Examples 1-3, except that the phosphorus component added was 1307 g of a mixture of orthophosphoric acid (87% by weight), pyrophosphoric acid (11.5% by weight) and triphosphoric acid (1.5% by weight). Distillation of the reaction mixture was begun after about 1 hour of refluxing, and was continued until about 2.7 liters of organic liquid was removed.

Examples 7-8

Catalysts of the formula $V_1P_{1.2}O_x$ were prepared according to the procedure of Example 6, except that distillation was commenced after about one half hour of refluxing, and was continued until about 6 liters of organic liquid was removed.

Examples 9-10

Catalysts of the formula $V_1P_{1.2}O_x$ were prepared according to the procedure of Example 6, except that about 8 liters of organic liquid were removed by distillation.

Examples 11-12

Catalysts of the formula $V_1P_{1.2}O_x$ were prepared according to the procedure of Example 6 except that about 11 liters of organic liquid were removed by distillation.

Comparative Examples 13-16

Catalysts of the formula $V_1P_{1.2}O_x$ were prepared according to the procedure of Example 6 except that no distillation of organic liquid was effected.

The catalysts described in Examples 1-16 were tested for the production of maleic anhydride from n-butane using a 20 cc fixed-bed reactor consisting of a 38 cm length of stainless steel tubing having an outer diameter of about 1.3 cm and having a full length 0.31 cm axial thermowell. The reactor was heated with a split stainless steel block furnace. Flasks for receiving the product maleic anhydride were mounted in ice water, and tail gases were routed to a Carle Analytical Gas Chromatograph III for analysis. Reaction conditions and results of the tests run are described in Table I. The results are stated in terms as follows:

$$\text{Single Pass Yield} = \frac{\text{Moles of Maleic Anhydride Formed}}{\text{Moles of Butane Fed}} \times 100$$

$$\text{Total Conversion} = \frac{\text{Moles of Butane Reacted}}{\text{Moles of Butane Fed}} \times 100$$

-continued $$\text{Selectivity} = \frac{\text{Single Pass Yield}}{\text{Total Conversion}}$$

As can be seen from the results reported in Table I, vanadium phosphorus mixed oxide containing catalysts prepared according to the process of the present invention, wherein at least 1.5 moles of organic liquid per mole of vanadium reacted are removed from the reaction medium during the reduction and/or reaction of vanadium, exhibit unexpectedly improved activity for the production of maleic anhydride from 4 carbon atom hydrocarbons such as butane, as compared to catalysts prepared absent such reaction liquid removal.

The liquid removed generally contains a portion of the oxidation products of the organic liquid utilized. As an example, when isobutanol was utilized as the organic liquid reaction medium for a catalyst preparation in which about 3 liters of isobutanol and byproducts (32.7 moles) were removed from the reaction medium in which 10 moles of vanadium were reacted for a removal mole ratio of about 3.3, the byproducts included about 46 g isobutyraldehyde (0.64 moles), 25 g acetone (0.43 moles) and 223 g water. The byproducts are easily separated from the desired organic liquid alcohol or glycol, and the purified organic liquid can be recycled for use in the catalyst preparation.

Both the uncalcined vanadium phosphorus catalyst precursors and the calcined vanadium phosphorus mixed oxide catalysts prepared according to the process of the present invention with organic liquid removal exhibit higher intrinsic surface areas as compared to their corresponding precursors and catalysts prepared without such organic liquid removal. For example, the intrinsic surface area of the catalyst precursor of Example 7 was 20% greater than the intrinsic surface area of the catalyst precursor of Comparative Example 14, and the intrinsic surface area of the calcined catalyst of Example 7 was nearly 200% greater than the intrinsic surface area of the calcined catalyst of Comparative Example 14. An increase in the intrinsic surface area for vanadium phosphorus mixed oxide catalysts of this type generally indicates an increase in oxidative catalytic activity. This increased activity is evidenced additionally by the results reported in Table I, in which increased conversions and yields of maleic anhydride are exhibited by catalysts prepared according to the present invention, as compared to the comparative examples.

Thus it should be apparent to those skilled in the art that the subject invention accomplishes the objects set forth above. It is to be understood that the subject invention is not to be limited by the examples set forth herein. These have been provided merely to demonstrate operability, and the selection of vanadium compounds, phosphorus compounds, liquid media, promoter element-containing compounds if any, hydrocarbon feedstocks and reaction conditions can be determined from the total specification disclosure provided without departing from the spirit of the invention herein disclosed and described, the scope of the invention including equivalent embodiments, modifications and variations that fall within the scope of the attached claims.

TABLE I

PRODUCTION OF MALEIC ANHYDRIDE FROM N—BUTANE OVER $V_1P_{1.2}O_x$ CATALYST

| Example Number | Temperature (°C.) | Contact Time (Seconds) | % Conversion | Maleic Anhydride % Yield | Maleic Anhydride % Selectivity | Removal Mole Ratio* |
|---|---|---|---|---|---|---|
| 1 | 402 | 2 | 80.8 | 52.0 | 64.3 | 10 |
| 2 | 402 | 2 | 76.6 | 51.4 | 67.1 | 10 |
| 3 | 409 | 2 | 81.6 | 53.3 | 65.4 | 10 |
| C4 | 400 | 2 | 66.6 | 45.4 | 68.1 | — |
| C5 | 400 | 2 | 66.3 | 46.4 | 70.1 | — |
| 6 | 423 | 1 | 88.5 | 51.6 | 58.3 | 3 |
| 7 | 418 | 1 | 82.6 | 52.3 | 63.3 | 6.5 |
| 8 | 401 | 2 | 87.0 | 58.6 | 67.3 | 6.5 |
| 9 | 420 | 1 | 78.9 | 47.5 | 60.2 | 8.7 |
| 10 | 409 | 2 | 83.4 | 53.5 | 64.1 | 8.7 |
| 11 | 420 | 1 | 85.7 | 46.7 | 54.5 | 12 |
| 12 | 400 | 2 | 84.6 | 55.8 | 66.1 | 12 |
| C13 | 420 | 1 | 60.0 | 33.5 | 55.9 | — |
| C14 | 419 | 1 | 74.2 | 48.2 | 64.9 | — |
| C15 | 407 | 2 | 64.9 | 41.2 | 63.5 | — |
| C16 | 402 | 2 | 69.8 | 46.9 | 67.2 | — |

*Moles organic liquid removed per mole of vanadium reacted in catalyst preparation

We claim:

1. A process for the production of maleic anhydride by the oxidation of 4 carbon atom hydrocarbons with molecular oxygen or an oxygen containing gas in the vapor phase at a reaction temperature of about 250° C. to about 600° C. in the presence of a catalyst containing the mixed oxides of vanadium and phosphorus, wherein said catalyst is prepared by
    (a) introducing a pentavalent vanadium compound into an organic liquid reaction medium selected from alcohols and glycols capable of reducing at least a portion of the vanadium to a valence state of about +4 in the absence of corrosive reducing agents;
    (b) introducing at least one pentavalent phosphorus compound into the reaction medium;
    (c) effecting reduction of the vanadium prior or subsequent to the addition of the phosphorus compound and reacting the vanadium with the phosphorus compound to form a catalyst precursor,
    (d) removing from the reaction medium at least 1.5 moles of the organic liquid including organic oxidation byproducts per mole of vanadium reduced or reacted during the reduction or reaction;
    (e) recovering the catalyst precursor from the reaction medium;
    (f) drying the catalyst precursor; and
    (g) calcining the catalyst precursor.

2. A process as in claim 1 wherein removing the organic liquid is by distillation.

3. A process as in claim 1 wherein said reduction is effected by heating at reflux conditions.

4. A process as in claim 1 wherein from 1.5 moles to about 15 moles of organic liquid is removed per mole of vanadium reduced or reacted.

5. A process as in claim 1 wherein said catalyst additionally comprises promoter elements selected from U, Co, Mo, Fe, Zn, Hf, Zr and mixtures thereof.

6. A process as in claim 1 wherein the phosphorous compound is added to the reaction medium before substantial reduction of vanadium occurs.

7. A process as in claim 1 wherein the phosphorus compound comprises orthophosphoric acid.

8. A process as in claim 1 wherein the phosphorus compound comprises a mixture of orthophosphoric acid and pyrophosphoric acid.

9. A process as in claim 1 wherein said organic liquid comprises isobutanol.

10. A process as in claim 1 wherein said organic liquid comprises ethylene glycol.

* * * * *